United States Patent [19]

Reed et al.

[11] 4,180,896

[45] Jan. 1, 1980

[54] BLOOD OXYGENATOR ASSEMBLY METHOD

[75] Inventors: Charles C. Reed; Denton A. Cooley, both of Houston; Russell G. Sharp, Sugar Land, all of Tex.

[73] Assignee: Texas Medical Products, Inc., Houston, Tex.

[21] Appl. No.: 952,020

[22] Filed: Oct. 16, 1978

Related U.S. Application Data

[62] Division of Ser. No. 865,476, Dec. 29, 1977.

[51] Int. Cl.$^2$ .............................................. A61M 1/03
[52] U.S. Cl. .................... 29/157 R; 422/46; 29/526 R
[58] Field of Search .............. 29/157 R, 526; 422/46, 422/47

[56] References Cited

U.S. PATENT DOCUMENTS

| | | | |
|---|---|---|---|
| 2,855,449 | 10/1958 | Owen | 422/201 X |
| 2,934,067 | 4/1960 | Calvin | 422/46 |
| 3,302,700 | 2/1967 | Dugan | 165/74 X |
| 3,468,631 | 9/1969 | Raible et al. | 422/46 |
| 3,768,977 | 10/1973 | Brumheld et al. | 422/46 |
| 3,769,162 | 10/1973 | Brumheld | 422/46 X |
| 3,853,479 | 12/1974 | Talonn | 422/46 |
| 3,888,412 | 6/1975 | Lindo | 165/74 X |
| 4,065,264 | 12/1977 | Lewin | 422/46 |
| 4,067,696 | 1/1978 | Curtis | 422/47 |

*Primary Examiner*—Barry S. Richman
*Attorney, Agent, or Firm*—H. Ross Workman; J. Winslow Young

[57] ABSTRACT

A blood oxygenator having two separable components one of which is disposable and the other of which is reusable and sterilizable. The disposable portion of the oxygenator is multichambered and provides an oxygenating chamber, a defoaming chamber and an arterial reservoir constructed so that blood will flow sequentially therethrough. The reusable member is constructed in the form of a cover for the oxygenator and has depending therefrom a heat exchanger for maintaining the temperature of the blood, the heat exchanger projecting telescopically into the oxygenating chamber. Defoaming is assisted by a cellular foam material rolled into a generally cylindrical configuration and having abutting faces which are bias cut so that the line formed by the abutting faces is not coaxial with the blood flow path. The device is assembled by inserting the defoaming material into the defoaming chamber of the open-topped oxygenator, then telescopically inserting the heat exchanger into the oxygenating chamber while placing the cover on the top of the oxygenator and thereafter removably securing the cover to the oxygenator.

2 Claims, 2 Drawing Figures

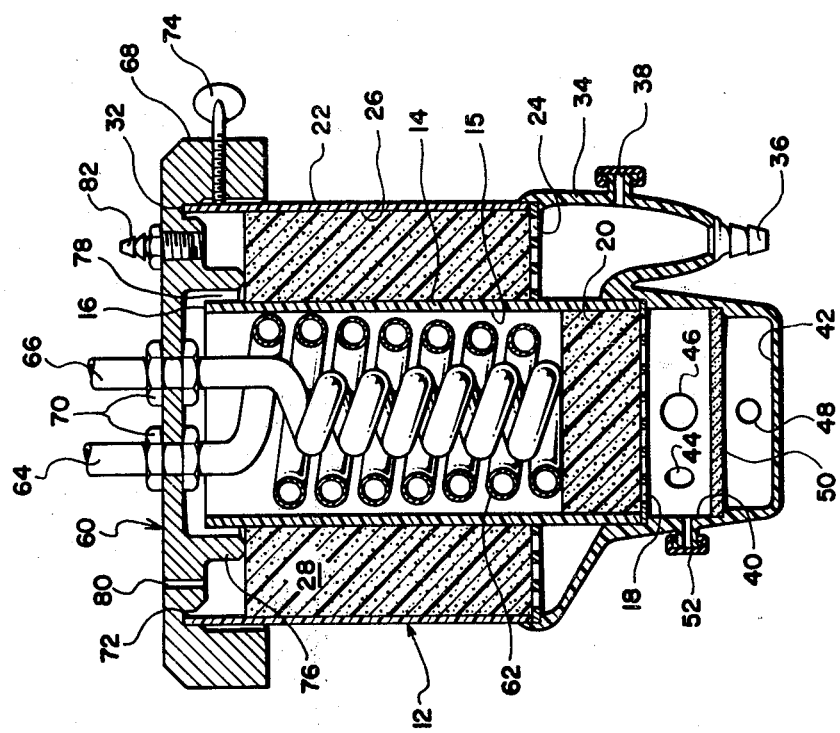
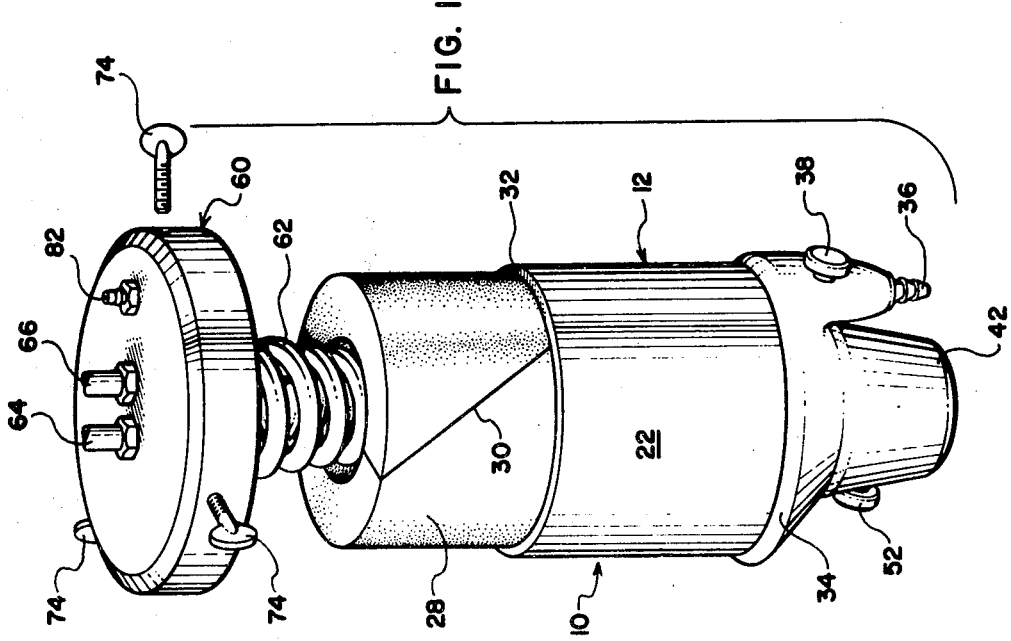

4,180,896

BLOOD OXYGENATOR ASSEMBLY METHOD

This is a division, of application Ser. No. 865,476, filed Dec. 29, 1977.

BACKGROUND

1. Field of the Invention

The present invention relates to extracorporeal blood treatment devices and more particularly to a blood oxygenator, an inexpensive portion of which can be disposed of and an expensive portion of which can be sterilized and reused.

2. The Prior Art

Cardiopulmonary bypass circuits have historically been used as an integral part of much modern heart surgery. The purpose for the cardiopulmonary bypass circuit is to permit blood to be pumped, oxygenated and defoamed extracorporeally.

Historically, a bubble oxygenator has been used in the circuit to replace temporarily the biological functions of the lungs. It was found, however, that conventional oxygenators when applied to a patient's blood extracorporeally developed a two-fold problem. First, gas trapped within the blood caused foaming which foam must be removed before the blood could be returned to the patient's body. Second, the comparatively long time duration with which the blood is conducted outside of the patient's body required a heat exchanger to maintain essential body temperature in the blood. In the earliest configuration of known devices, the heat exchanger and the oxygenator were two separate devices in the same circuit.

More recently, however, oxygenators have been utilized which combine the heat exchanger and the oxygenator functions in a single device. Either with or without a heat exchanger, conventional oxygenators typically have convoluted flow paths attenuated with a plurality of filters, dispersion plates and the like. The conventional oxygenators mentioned tend to trap blood in the circuit in such a manner as to make it impossible to completely clean or remove the blood from the oxygenator and attendant heat exchanger. Accordingly, the entire oxygenator must be disposed of and cannot be safely reused.

Often, one of the more expensive and complicated portions of the extracorporeal blood circuit is the heat exchanger. It has been found on prior art devices that those heat exchangers which are an integral part of the oxygenators are disposable therewith thereby incurring significant unnecessary costs.

It would be desirable, therefore, to provide an improved blood oxygenator with a sterilizable and reusable heat exchange element easily used with and separable from a disposable portion of the oxygenator containing the more complex and nonsterilizable blood circuit.

BRIEF DESCRIPTION OF THE INVENTION

The present invention comprises novel and unobvious blood oxygenator device and method which accommodates coupling a sterilizable and reusable heat exchange member with a disposable oxygenator device in a simplified and uncomplicated manner. After the oxygenator has been used, the more expensive elements can be simply and easily cleansed and sterilized and the less expensive portions can be easily disposed thereby minimizing expense and maximizing efficiency of the system.

It is, therefore, a primary object of the present invention to provide an improved blood oxygenator device.

It is another valuable object of the present invention to provide an improved assembly for oxygenating blood including a defoaming insert which can be rapidly and easily inserted into the oxygenator.

It is another desirable object of the present invention to provide an improved heat exchanger-oxygenator combination having improved oxygenation efficiency.

These and other valuable objects and features of the present invention will become more fully apparent from the following description and appended claims taken in conjunction with the accompanying drawings.

BRIEF DESCRIPTION OF THE DRAWING

FIG. 1 is an exploded perspective view of a preferred heat exchanger embodiment of the invention.

FIG. 2 is a longitudinal cross section of the embodiment of FIG. 1 in a fully assembled form.

DETAILED DESCRIPTION OF THE PREFERRED EMBODIMENT

Attention is now directed to the preferred embodiment of the oxygenator of the present invention illustrated in the drawing. The oxygenator generally designated 10 comprises a multichambered receptacle generally designated 12 which, in the illustrated embodiment, is generally cylindrical in configuration. Referring particularly to FIG. 2, the receptacle 12 includes an oxygenating chamber 14 which is cylindrical in configuration and is open at the top 16. The bottom 18 of the oxygenating chamber 14 is constructed as a perforated disc to permit blood and oxygen to enter into the oxygenating chamber from the bottom. A layer of cellular foam 20 provides an enlarged surface area which maximizes the oxygen-blood contact and thereby improves oxygenation. It further disperses the blood so that it will rise more uniformly through the oxygenating chamber 14.

A defoaming chamber 22 circumscribes the upper portion of the oxygenating chamber 14 and is configurated generally as an annular sleeve. The defoaming receptacle 22 is mounted upon the oxygenating receptacle 14 with a perforated annular plate 24. Securement of the plate 24 and disc 18 is effected with a fluid-tight weld. The wall of the oxygenating chamber 14 forms the inside surface of the defoaming receptacle 22 and thus an annular space 26 exists between the wall of the defoaming chamber 22 and the wall of the oxygenating chamber 14. The space 26 is adapted to receive defoaming insert 28 (see FIG. 1). Defoaming insert 28 is initially a flat silicon-coated polyurethane foam. The edges of the foam insert are bias cut so that when the insert is rolled into a generally cylindrical configuration as illustrated in FIG. 1, the bias-cut edges form a diagonal line 30 running from the top of the insert to the bottom of the insert. The slope of the diagonal line 30 is intentionally selected so as to be non-aligned with the blood flow path and thus minimize blood channeling therealong.

It will be observed by reference to FIG. 2 that in the assembled condition, the insert 28 is situated below the upper edge 16 of the oxygenating chamber 14. It is also observed that the upper edge 32 of the defoaming chamber 22 is normally above the upper edge 16 of the oxygenating chamber 14. Thus it can be observed that as blood rises in the oxygenating chamber 14, it will flow over the top 16 and into the defoaming chamber 22.

Thereafter, the blood will traverse downwardly and pass through the annular plate 24.

Oxygenated blood emerging through the annular plate 24 is accumulated in arterial reservoir 34. The arterial reservoir provides a safety feature in that the reservoir helps prohibit the accidental transmission of air into a patient by providing a second reservoir of blood which permits a physician or perfusionist to prevent the flow of air into a patient in the event the venous flow of blood into the oxygenator is abruptly terminated for some reason. The arterial reservoir has an exterior configuration which is complementary to the periphery of the defoaming chamber 22 and is welded or otherwise suitably secured thereto. Thus blood can be collected over the entire surface area of the plate 24. The blood collected and stored within the arterial reservoir 34 is delivered to the patient through nipple 36 in accordance with known techniques. A sampling port 38 may be utilized to permit selective blood sampling at the outlet of the oxygenator prior to return to the patient.

In the illustrated embodiment, a blood inlet chamber 40 and an oxygen inlet chamber 42 are integrally molded with the arterial reservoir 34. Cardiotomy blood enters the chamber 40 at port 44 and patient venous blood enters the chamber 40 at port 46. Oxygen enters the chamber 42 through the port 48. It is observed that the chamber 42 and the chamber 40 are separated by a sparger plate 50. Sparger plate 50 diffuses the oxygen entering at 48 into a large number of very small bubbles and causes the oxygen bubbles to pass generally uniformly into the chamber 40 and to be there mixed with the blood entering at 44 and 46. Patient inlet blood may, if desired, be sampled at the port 52.

In operation, the blood entering through the ports 42 and 46 is exposed to oxygen rising through the sparger plate 50 and thereafter passes through the perforated disc 18 into the oxygenating chamber 14. The foam 20 assists in providing an enlarged surface area for maximizing oxygenation of the blood. As the blood rises to the top 16 of the oxygenator chamber 14, it spills over into the defoaming chamber 22 and passes through the cellular foam cylinder 28 downward through the perforated plate 24 and into the arterial chamber 34. Thereafter, the blood is returned to the patient.

In order to complete the oxygenator system it is necessary to provide a heat exchange medium to ensure that the blood returned to the patient closely approximates the appropriate body temperature. To provide this function, a heat exchanger assembly generally designated 60 is provided. The assembly 60 comprises a heat exchange coil 62 which is configurated so as to nest within the hollow 15 of the heat exchange chamber 14 and to be thus immersed in the blood flowing through the oxygenator. Heat exchanger 62 is preferably formed of stainless steel or other suitable reusable and sterilizable material. Stainless steel has been found effective because of its heat radiation properties and its resistance to contamination. The heat exchanger includes an inlet tube 64 and an outlet tube 66 through which heated fluids such as water are conducted. Notably, in the illustrated embodiment, the heat exchanger coils through a double inverted cone shape. While any suitable heat exchanger configuration could be used, the illustrated embodiment has been found to be surprisingly effective in reducing the boundary layer effect between the blood and oxygen as it rises through the oxygenating chamber 14. Moreover, the reduction of the boundary layer effect is observed without substantial turbulence which tends to increase blood foaming and hemolysis. Accordingly, with the heat exchanger directly exposed to the blood as it passes through the oxygenating chamber 14, a highly effective oxygenation process has been effected.

Tubes 64 and 66 are mounted in oxygenator cover 68. While any suitable mounting means could be used, conventional threaded hex nuts 70 have been found adequate. The cover 68 is likewise preferably formed of stainless steel and is interiorly constructed so as to close oxygenator 12 at its normally open end. In order to facilitate closure, the cover 68 has an annular recess 72 into which the upper edge 32 of defoaming chamber 22 is inserted. Thumb screws 74 or other suitable attachment means may be used to removably mount the oxygenator 12 to the heat exchange assembly 60.

Cover 68 has an annular downwardly projecting ridge 76 which engages defoaming insert 28 and urges the insert into its proper nesting relationship within the defoaming chamber 22. It is observed that the annular ridge 76 is spaced from the oxygenating chamber 14 as at 78 so as to permit free flow of blood therebetween as the blood traverses from the inside of the oxygenating chamber to the defoaming chamber 22. In order to remove excess gases accumulating in the chamber, a vent 80 is formed in the cover 68 to permit escape of the gases.

The cover 68 is further provided with a nipple 82 which is typically used to prime the oxygenator immediately prior to use.

Significantly, the cover 68 and the heat exchanger 62 are detachably associated with the disposable multichambered oxygenator 12. Thus, by releasing the thumb screws 74 (FIG. 1) the cover 68 and appended heat exchanger set 62 may be easily removed from the oxygenator which may thereafter be discarded. The heat exchanger may be easily cleansed and sterilized in an autoclave or the like and is thereafter ready for reuse by merely nesting the heat exchanger 62 is a corresponding oxygenating receptacle 14.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of assemblying a blood oxygenator having (1) a disposable multichambered receptacle including an oxygenating chamber, a defoaming chamber integral with and in the immediate proximity of at least a portion of said oxygenating chamber, means for communicating blood flow from said oxygenating chamber to said defoaming chamber and an arterial reservoir and (2) a reusable sterilizable heat exchanger for exchanging heat with blood passing through said oxygenating chamber comprising an oxygenator cover and a heat exchanger means projecting therefrom, the method comprising the steps of:

placing a defoaming means insert into the defoaming chamber such that the insert conforms to the configuration of the defoaming chamber;

telescopically interposing at least a portion of the heat exchanger means into the oxygenating chamber so that a heat exchanging portion thereof will be immersed in blood flowing through the oxygenating chamber; and removably securing the oxygenator cover to the receptacle.

2. A method as defined in claim 1 further comprising providing a cylindrical configuration to the defoaming chamber and rolling a flexible defoaming means insert into a configuration of a cylindrical sleeve and abutting ends of the insert along a diagonal line for insertion thereof into the defoaming chamber.

* * * * *